(12) United States Patent
Ueda et al.

(10) Patent No.: US 9,670,111 B2
(45) Date of Patent: Jun. 6, 2017

(54) CATALYST FOR PRODUCING ISOBUTYLENE AND METHOD FOR PRODUCING ISOBUTYLENE USING THE SAME

(71) Applicants: NATIONAL UNIVERSITY CORPORATION HOKKAIDO UNIVERSITY, Hokkaido (JP); MITSUBISHI RAYON CO., LTD., Tokyo (JP)

(72) Inventors: Wataru Ueda, Sapporo (JP); Toru Murayama, Sapporo (JP); Ken Ooyachi, Otake (JP); Wataru Ninomiya, Otake (JP); Toshiya Yasukawa, Otake (JP)

(73) Assignees: NATIONAL UNIVERSITY CORPORATION HOKKAIDO UNIVERSITY, Sapporo-shi (JP); MITSUBISHI RAYON CO., LTD., Chiyoda-ku (JP)

( * ) Notice: Subject to any disclaimer, the term of this patent is extended or adjusted under 35 U.S.C. 154(b) by 90 days.

(21) Appl. No.: 14/416,924

(22) PCT Filed: Sep. 18, 2013

(86) PCT No.: PCT/JP2013/075130
§ 371 (c)(1),
(2) Date: Jan. 23, 2015

(87) PCT Pub. No.: WO2014/046118
PCT Pub. Date: Mar. 27, 2014

(65) Prior Publication Data
US 2015/0202597 A1  Jul. 23, 2015

(30) Foreign Application Priority Data
Sep. 18, 2012  (JP) .................................. 2012-204035

(51) Int. Cl.
*B01J 23/20* (2006.01)
*C07C 1/24* (2006.01)
(Continued)

(52) U.S. Cl.
CPC ............... *C07C 1/24* (2013.01); *B01J 23/002* (2013.01); *B01J 23/28* (2013.01); *B01J 23/30* (2013.01);
(Continued)

(58) Field of Classification Search
CPC ........ B01J 21/063; B01J 23/002; B01J 23/20; B01J 23/28; B01J 23/30; B01J 2523/47;
(Continued)

(56) References Cited

U.S. PATENT DOCUMENTS 3,505,118 A * 4/1970 Mehra ................. H01M 4/9016
423/594.5
3,821,324 A  6/1974 Bertus
(Continued)

FOREIGN PATENT DOCUMENTS

CN  10-2603501  * 7/2012 ............. C07C 45/35
GB  650 475  2/1951
(Continued)

OTHER PUBLICATIONS

Murayama, T., et al., "Synthesis of porous and acidic complex metal oxide catalyst based on group 5 and 6 elements", Catalysis Today, vol. 185, No. 1, pp. 224-229, (2012).
(Continued)

*Primary Examiner* — Patricia L Hailey
(74) *Attorney, Agent, or Firm* — Oblon, McClelland, Maier & Neustadt, L.L.P.

(57) ABSTRACT

Provided are a catalyst whereby isobutylene can be produced at high yield in a lower-temperature environment, and a method for producing isobutylene using the catalyst. The
(Continued)

catalyst for producing isobutylene is an oxide including at least one element selected from molybdenum and tungsten, and at least one element selected from tantalum, niobium, and titanium.

9 Claims, 1 Drawing Sheet

(51) Int. Cl.
- *B01J 23/28* (2006.01)
- *B01J 23/30* (2006.01)
- *B01J 37/10* (2006.01)
- *B01J 23/00* (2006.01)

(52) U.S. Cl.
CPC ............ *B01J 37/10* (2013.01); *B01J 2523/00* (2013.01); *C07C 2521/04* (2013.01); *C07C 2521/06* (2013.01); *C07C 2521/08* (2013.01); *C07C 2521/12* (2013.01); *C07C 2523/20* (2013.01); *C07C 2523/28* (2013.01); *C07C 2523/30* (2013.01)

(58) Field of Classification Search
CPC  B01J 2523/56; B01J 2523/57; B01J 2523/68; B01J 2523/69; C07C 2521/06; C07C 2523/20; C07C 2523/28; C07C 2523/30
USPC .......................................... 502/308, 309, 311
See application file for complete search history.

(56) References Cited

U.S. PATENT DOCUMENTS

| | | | |
|---|---|---|---|
| 3,933,933 A | 1/1976 | Bertus | |
| 4,164,519 A | 8/1979 | Bertus | |
| 4,333,858 A * | 6/1982 | Decker | B01J 23/002 502/241 |
| 5,510,309 A * | 4/1996 | Chang | B01J 23/30 208/46 |
| 5,637,546 A * | 6/1997 | Tenten | B01J 23/002 502/311 |
| 2005/0054869 A1* | 3/2005 | Lugmair | B01J 23/002 558/323 |
| 2009/0292086 A1* | 11/2009 | Shin | B01J 23/002 526/101 |
| 2011/0172475 A1 | 7/2011 | Peters et al. | |

FOREIGN PATENT DOCUMENTS

| | | |
|---|---|---|
| JP | 163171 | 6/1944 |
| JP | 11 114418 | 4/1999 |
| JP | 11 514337 | 12/1999 |
| WO | 2011 085223 | 7/2011 |

OTHER PUBLICATIONS

Omata, C., et al., "Hydrothermal synthesis of W-Nb complex metal oxides and their application to catalytic dehydration of glycerol to acrolein", Catalysis Today, vol. 201, pp. 7-11, (2013).

AI, M., "Kakushu Tungsten-kei Fukugo Nigen Sankabutsu no San Enki-sei", Dai 48 Kai Shokubai Toronkai (A) Koen Yokoshu, pp. 260-261, (Sep. 21, 1981) (with English abstract).

Taylor, J. D., et al., "Dehydration of Fermented Isobutanol for the Production of Renewable Chemicals and Fuels", Topics in Catalysis, vol. 53, No. 15-18, pp. 1224-1230, (2010).

International Search Report Issued Dec. 17, 2013 in PCT/JP13/075130 Filed Sep. 18, 2013.

* cited by examiner

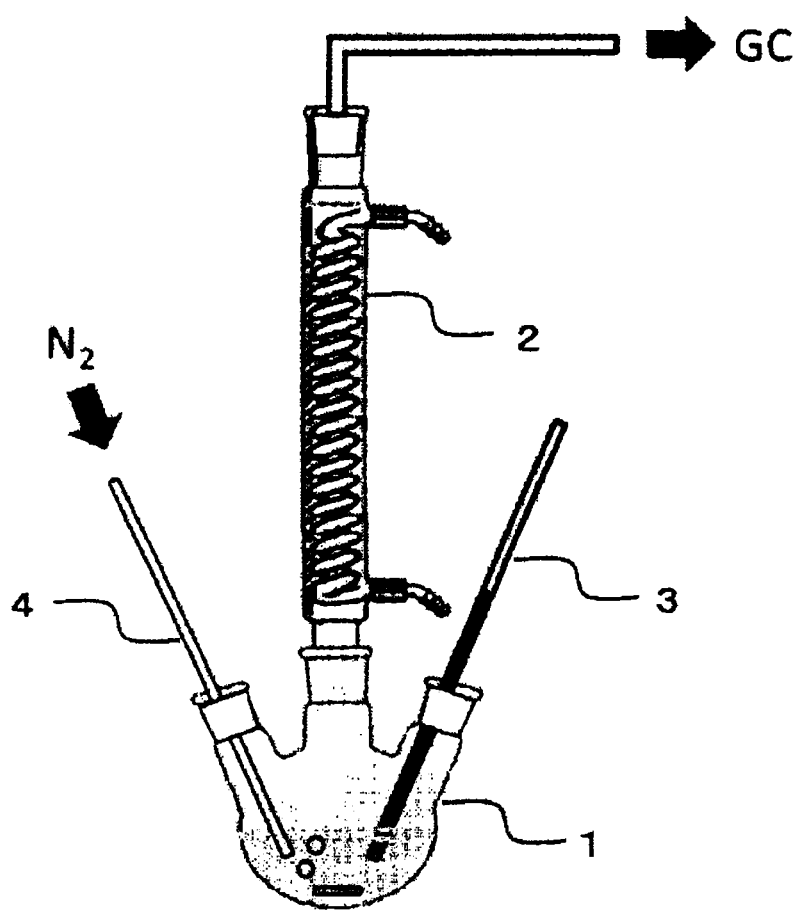

CATALYST FOR PRODUCING ISOBUTYLENE AND METHOD FOR PRODUCING ISOBUTYLENE USING THE SAME

TECHNICAL FIELD

The present invention relates to a catalyst for producing isobutylene and a method for producing isobutylene using the same.

BACKGROUND ART

The majority of chemical products are manufactured using petroleum as a raw material. In recent years, however, the depletion of petroleum is concerned and carbon dioxide generated at the time of burning petroleum is considered as a cause of global warming. Hence, biomass-derived chemicals called carbon neutral are expected as a substitute of petroleum.

Isobutylene is one of important chemical raw materials which are converted into ethyl tert-butyl ether (ETBE), p-xylene, methyl methacrylate (MMA) and the like.

Isobutanol is produced as a byproduct at the time of producing 2-ethylhexanol by oxo reaction using water gas and propylene as raw materials.

On the other hand, isobutanol is known to be produced by the fermentation of glucose and exemplified as one of the biomass-derived raw materials. For example, it is described in Non-Patent Literature 1 and Patent Literature 1 that isobutylene can be produced by the dehydration of isobutanol.

CITATION LIST

Patent Literature

Patent Literature 1: JP 11-514337 W

Non-Patent Literature

Non-Patent Literature: Topics in Catalysis (2010) 53, 1224-1230

SUMMARY OF THE INVENTION

Problem to be Solved by the Invention

The above-mentioned reaction is an endothermic reaction since it is a dehydration reaction, and thus the reaction requires more thermal energy in the case of being conducted in a high temperature region. A reaction in a lower temperature region is desired in order to cut down the amount of thermal energy used from the viewpoint of energy saving. In Non-Patent Literature 1, it is required to set the reaction temperature to 300° C. in order to achieve a high conversion rate although γ-alumina is used as a catalyst and thus selectivity is high. In Patent Literature 1, the development of catalyst is desired which can achieve a high conversion rate at a lower temperature and high selectivity although niobic acid and silica alumina are used as a catalyst and thus the reaction temperature required to achieve a high conversion rate is lower than the case of using γ-alumina.

The invention is made to solve the above-mentioned problem. In other words, an object of the invention is to provide a catalyst which can produce a high yield of isobutylene in a lower temperature region and a method for producing isobutylene using the same.

Means for Solving Problem

A catalyst for producing isobutylene according to the invention is an oxide containing at least one element selected from a group A and at least one element selected from a group B, and the group A herein consists of molybdenum and tungsten and preferably tungsten and the group B herein consists of tantalum, niobium, and titanium. The oxide is preferably a complex oxide. Moreover, a ratio (A/B) of a total A of the numbers of moles of molybdenum and tungsten to a total B of the numbers of moles of tantalum, niobium, and titanium is preferably from 0.1 to 10.

Effect of the Invention

According to the invention, it is possible to provide a catalyst which can produce a high yield of isobutylene in a lower temperature region and a method for producing isobutylene using the same.

BRIEF DESCRIPTION OF DRAWING

FIG. 1 is a schematic diagram illustrating an example of a reaction apparatus used in a liquid phase reaction.

MODE(S) FOR CARRYING OUT THE INVENTION

The catalyst for producing isobutylene according to the invention is an oxide containing at least one element selected from a group A and at least one element selected from a group B.

Group A: molybdenum and tungsten
Group B: tantalum, niobium, and titanium

The catalyst for producing isobutylene according to the invention can be used as a catalyst, for example, in the method for producing isobutylene by the dehydration of isobutanol.

The catalyst according to the invention is an oxide containing one or more elements selected from molybdenum and tungsten and one or more elements selected from tantalum, niobium, and titanium. It is presumed that the one or more elements selected from molybdenum and tungsten have a function to form the backbone of the catalyst structure and the one or more elements selected from tantalum, niobium, and titanium have a function to form the active site structure. By virtue of this, it is possible to produce a high yield of isobutylene even in a lower temperature region, for example, in the case of producing isobutylene by the dehydration of isobutanol using the catalyst described above.

Tungsten is preferred between molybdenum and tungsten since the activity is more improved.

The element ratio ((Mo+W)/(Ta+Nb+Ti)) of one or more elements selected from molybdenum and tungsten to one or more elements selected from tantalum, niobium, and titanium which are contained in the oxide is not particularly limited but is preferably 0.01 or more and 10 or less. The optimal element ratio is different depending on the combination of the elements to be used and, for example, the element ratio (Mo+W)/Ta is more preferably 1.0 or more and 9.0 or less. The element ratio (Mo+W)/Nb is more preferably 0.25 or more and 4.0 or less. The element ratio (Mo+W)/Ti is more preferably 2.0 or more and 8.0 or less. The catalytic activity becomes more favorable when the element ratio ((Mo+W)/(Ta+Nb+Ti)) is within the above range. Meanwhile, it is preferable that the element ratio be within the above range even in a case in which the oxide contains only either of molybdenum or tungsten and/or only one of tantalum, niobium, and titanium. It is preferable that the element ratio (W/Ta) be within the above range, for example, even in a case in which the oxide contains tungsten and tantalum but does not contain molybdenum, niobium, and titanium. In addition, the above element ratio is a value calculated from the amount of each of the elements charged as the raw materials.

The oxide containing one or more elements selected from molybdenum and tungsten and one or more elements selected from tantalum, niobium, and titanium may be a complex oxide of the respective elements or a mixture of oxides of the respective elements. However, the oxide is preferably a complex oxide of the respective elements. Meanwhile, it is possible to confirm that the oxide is a complex oxide of the respective elements by X-ray diffraction.

In the complex oxide constituted by one or more elements selected from molybdenum and tungsten and one or more elements selected from tantalum, niobium, and titanium, oxygen which is a constituent of the complex oxide is present at the atomic ratio of oxygen required to satisfy the valence of each component.

The catalyst according to the invention may be supported on a support. The support is not particularly limited, and examples thereof may include alumina, silica, silica alumina, titania, and zirconia. Only one kind of these may be used, or two or more kinds thereof may be used concurrently.

Hereinafter, an example of a method for producing the catalyst according to the invention will be described.

It is possible to use an oxide, a sulfate salt, a nitrate salt, a carbonate salt, an oxalate salt, a hydroxide, an ammonium salt, an organic acid salt, a halide and the like of each of the elements as the raw materials of the catalyst components. It is possible to use, for example, ammonium paramolybdate and molybdenum trioxide as the molybdenum raw material. It is possible to use, for example, ammonium paratungstate and ammonium metatungstate as the tungsten raw material. It is possible to use, for example, tantalum acid as the tantalum raw material. It is possible to use, for example, niobic acid, niobium hydrogen oxalate, and ammonium niobium oxalate as the niobium raw material. It is possible to use, for example, titanium (III) sulfate as the titanium raw material. Only one kind of the raw materials of the catalyst components may be used for each element or two or more kinds thereof may be used in combination.

These raw materials are dissolved or dispersed in a liquid. It is possible to use water, an organic solvent such as alcohols such as methanol, ethanol, 2-propanol, and the like as the liquid. Only one kind of these liquids may be used or two or more kinds thereof may be used concurrently.

The hydrothermal synthesis is performed using the solution or dispersion thus obtained. The hydrothermal synthesis can be conducted in an autoclave. The temperature for hydrothermal synthesis is preferably 125° C. or higher and 300° C. or lower, more preferably 150° C. or higher and 250° C. or lower, and even more preferably 175° C. or higher and 230° C. or lower. The solid matter obtained by the hydrothermal synthesis is preferably washed with water, an organic solvent or the like in order to remove undesired dissolved components. After the washing, filtering is performed in order to separate the solid matter from the solvent.

Thereafter, the solid matter thus obtained is subjected to the heat treatment. The atmosphere gas used in the heat treatment is not particularly limited, and it is possible to use, for example, air, nitrogen, argon, carbon dioxide, and steam. Only one kind of these atmosphere gases may be used or two or more kinds thereof may be used concurrently. The temperature for heat treatment is preferably 300° C. or higher and 1000° C. or lower, more preferably 400° C. or higher and 800° C. or lower, and even more preferably 500° C. or higher and 700° C. or lower. The time for heat treatment is preferably 10 minutes or longer and 10 hours or shorter, more preferably 30 minutes or longer and 5 hours or shorter, and even more preferably 1 hour or longer and 2 hours or shorter. In this manner, it is possible to obtain a catalyst.

The catalyst thus obtained can be molded if necessary and then used. As a method for molding the catalyst, for example, a method is exemplified in which an additive is mixed with the catalyst if necessary, and then the mixture is molded into an arbitrary shape such as a spherical shape, a ring shape, a cylindrical shape, or a star shape using a powder molding machine such as a tablet molding machine, an extrusion molding machine, or a tumbling granulator. In addition, the catalyst thus obtained may be ground to be used as powder.

Next, a method for producing isobutylene from isobutanol using the catalyst described above will be described. The method for producing isobutylene according to the invention is a method for producing isobutylene by the dehydration of isobutanol and uses the catalyst for producing isobutylene described above.

Isobutylene can be produced, for example, by bringing gaseous isobutanol, which is a raw material, into the gas phase contact with the catalyst described above in an inert gas stream so as to dehydrate.

It is preferable to use biomass-derived isobutanol as isobutanol of the raw material from the viewpoint of environmental protection. Examples of the biomass-derived isobutanol may include isobutanol obtainable by the fermentation of glucose.

The concentration of isobutanol which is the reaction raw material in the source gas can be freely selected. It is possible to use nitrogen, carbon dioxide, steam, or the like as the inert gas. Only one kind of these inert gases may be used or two or more kinds thereof may be used concurrently. The reaction pressure is preferably from the normal pressure to 1 MPaG and more preferably from the normal pressure to 0.5 MPaG. The reaction temperature can be selected in the range of from 100 to 400° C. but is preferably from 100 to 250° C., more preferably from 100 to 200° C., and even more preferably from 100 to 150° C. from the viewpoint of sufficiently obtaining the effect of the invention.

On the other hand, it is also possible to produce isobutylene by the dehydration of liquid isobutanol through the liquid phase reaction. Isobutanol which is the reaction raw material in the liquid phase raw material can also be diluted with an appropriate solvent, but the reaction may be conducted using 100% by mass of isobutanol without diluting. An organic solvent may be used for the concentration adjustment of isobutanol. In addition, an inert gas may be supplied in order to remove oxygen, and it is possible to use nitrogen, carbon dioxide, or the like. The reaction pressure is not particularly limited but is preferably from the reduced pressure to 1 MPaG and more preferably from −0.001 MPaG to 0.5 MPaG. The reaction temperature can be selected from the boiling point of isobutanol or lower but is preferably near the boiling point from the viewpoint of improving the activity.

EXAMPLES

Hereinafter, the invention will be specifically described with reference to Examples on the dehydration of isobutanol, but the invention is not limited to these Examples.

The analyses of the source gas and the product were performed using the gas chromatography. Meanwhile, the conversion rate of isobutanol and the selectivity and yield of isobutylene to be produced are defined as follows.

Conversion rate of isobutanol (%)=($\beta/\alpha$)×100

Selectivity of isobutylene (%)=($\gamma/\delta$)×100

Yield of isobutylene (%)=($\beta/\alpha$)×($\gamma/\delta$)×100

Decomposition speed of isobutanol (mmol/h·g)=$\delta$/($a$×$b$)

Here, $\alpha$ denotes the number of moles of isobutanol supplied, $\beta$ denotes the number of moles of isobutanol reacted, $\gamma$ denotes the number of moles of isobutylene produced. In addition, $\delta$ denotes the number of moles of the total reaction products (isobutylene, 1-butene, cis-2-butene, trans-2-butene and n-butane) detected by the gas chromatography. In addition, a denotes the reaction time (h), and b denotes the amount of catalyst (g).

Example 1

The solution prepared by dissolving 2.0 mmol of ammonium metatungstate as tungsten in 20 ml of water and the dispersion prepared by dispersing 2.0 mmol of tantalic acid as tantalum in 25 ml of water were introduced into an autoclave and subjected to the hydrothermal synthesis at 175° C. for 72 hours. This was filtered, and the solid substance was subjected to the heat treatment at 500° C. for 2 hours under a nitrogen gas stream so as to prepare a catalyst.

The catalyst thus obtained was ground to obtain a powder. Quartz sand was added to 0.2 g of the powder so as to have a volume of 4 ml, and then the resultant was packed in a reactor having an inner diameter of 12.8 mm. As the material gas, nitrogen and isobutanol (as gas) were allowed to flow at 20 mol/min and 0.304 ml/min, respectively, and allowed to react at a reaction temperature of 150° C. The results are presented in Table 1.

Example 2

The same operation as in Example 1 was conducted except using the solution prepared by dissolving 2.7 mmol of ammonium metatungstate as tungsten in 20 ml of water. The results are presented in Table 1.

Example 3

The same operation as in Example 1 was conducted except using the solution prepared by dissolving 6.0 mmol of ammonium metatungstate as tungsten in 20 ml of water. The results are presented in Table 1.

Example 4

The same operation as in Example 1 was conducted except using the solution prepared by dissolving 2.7 mmol of ammonium paramolybdate instead of ammonium metatungstate as molybdenum in 20 ml of water. The results are presented in Table 1.

Example 5

The solution prepared by dissolving 0.5 mmol of ammonium paramolybdate instead of ammonium metatungstate as molybdenum in 20 ml of water was used. In addition, the dispersion prepared by dispersing 2.0 mmol of ammonium niobium oxalate instead of tantalic acid as niobium in 20 ml of water was used. The same operation as in Example 1 was conducted except these operations. The results are presented in Table 1.

Example 6

The solution prepared by dissolving 5.0 mmol of ammonium metatungstate as tungsten in 20 ml of water, the dispersion prepared by dispersing 0.814 mmol of titanium (III) sulfate as titanium in 25 ml of water, and further 5 mmol of oxalic acid were introduced into an autoclave and subjected to the hydrothermal synthesis at 175° C. for 24 hours. This was filtered, and the solid substance was subjected to the heat treatment at 500° C. for 2 hours under a nitrogen gas stream so as to prepare a catalyst. The same operation as in Example 1 was conducted except those operations. The results are presented in Table 1.

Comparative Example 1

The same operation as in Example 1 was conducted except using $\gamma$-alumina (trade name: AL3996 manufactured by BASF) as the catalyst. The results are presented in Table 1.

Comparative Example 2

The same operation as in Example 1 was conducted except using tantalic acid as the catalyst. The results are presented in Table 1.

Comparative Example 3

The same operation as in Example 1 was conducted except using niobic acid as the catalyst. The results are presented in Table 1.

TABLE 1

| | Catalyst | Elapsed reaction time (hr) | Conversion rate (%) | Selectivity (%) | Yield (%) |
|---|---|---|---|---|---|
| Example 1 | WTaO (W/Ta = 1) | 3.5 | 100.0 | 89.6 | 89.6 |
| Example 2 | WTaO (W/Ta = 1.35) | 2.8 | 76.3 | 80.1 | 61.1 |
| Example 3 | WTaO (W/Ta = 3) | 3.8 | 100.0 | 87.0 | 87.0 |
| Example 4 | MoTaO (Mo/Ta = 1.35) | 2.5 | 10.6 | 90.7 | 9.6 |
| Example 5 | MoNbO (Mo/Nb = 0.25) | 2.5 | 28.8 | 81.8 | 23.6 |
| Example 6 | WTiO (W/Ti = 6.14) | 5.0 | 100.0 | 82.5 | 82.5 |
| Comparative Example 1 | $\gamma$-alumina | 2.6 | 0.0 | — | 0.0 |

TABLE 1-continued

| | Catalyst | Elapsed reaction time (hr) | Conversion rate (%) | Selectivity (%) | Yield (%) |
|---|---|---|---|---|---|
| Comparative Example 2 | Tantalic acid | 1.5 | 4.3 | 82.1 | 3.5 |
| Comparative Example 3 | Niobic acid | 1.5 | 1.2 | 61.2 | 0.7 |

Example 7

As illustrated in FIG. 1, 20 ml of isobutanol was introduced into a three-necked flask 1, a condenser tube 2, a thermometer 3, and a nitrogen introduction line 4 were provided thereto, a nitrogen gas was allowed to flow into the flask at 20 ml/min, and the temperature inside the flask was raised to 105° C. under a normal pressure. To the flask, 0.2 g of the catalyst prepared in Example 6 was added and the reaction was conducted for 5 hours. The gas at the outlet of the condenser tube was analyzed. The results are presented in Table 2.

Example 8

The same operation as in Example 7 was conducted except using the catalyst prepared in Example 1. The results are presented in Table 2.

Comparative Example 4

The same operation as in Example 7 was conducted except using the catalyst used in Comparative Example 1. The results are presented in Table 2.

TABLE 2

| | Catalyst | Decomposition speed (mmol/h · g) | Selectivity (%) |
|---|---|---|---|
| Example 7 | WTiO (W/Ti = 6.14) | 0.337 | 89.4 |
| Example 8 | WTaO (W/Ta = 1) | 0.027 | 86.9 |
| Comparative Example 4 | γ-alumina | 0.000 | — |

As presented in Table 1, it was possible to obtain a high yield of isobutylene even by the reaction in a low temperature region of 150° C. in Examples.

As presented in Table 2, it was possible to obtain isobutylene even by the reaction in a low temperature region of 105° C. in Examples.

According to the invention, it is possible to provide a catalyst which can produce a high yield of isobutylene in a lower temperature region.

This application is based upon and claims the benefit of priority of the prior Japanese Patent Application No. 2012-204035, filed on Sep. 18, 2012, the entire contents of which are incorporated herein by reference.

Hereinbefore, the invention has been described with reference to embodiments and Examples, but the invention is not intended to be limited to the above embodiments and Examples. It should be understood by those skilled in the art that various modifications could be made to the configuration and details of the invention without departing from the scope of the invention.

The invention claimed is:

1. A catalyst for producing isobutylene which is an oxide consisting of tungsten and at least one element selected from a group B Group B: tantalum, niobium, and titanium.

2. The catalyst for producing isobutylene according to claim 1, wherein the oxide is a complex oxide.

3. The catalyst for producing isobutylene according to claim 1, wherein a ratio (A/B) of a A of the numbers of moles of tungsten to a total B of the numbers of moles of tantalum, niobium, and titanium is from 0.1 to 10.

4. The catalyst for producing isobutylene according to claim 1, wherein B is tantalum.

5. The catalyst for producing isobutylene according to claim 4, wherein a ratio (A/B) of a A of the numbers of moles of tungsten to a total B of the numbers of moles of tantalum is from 1.0 to 9.0.

6. The catalyst for producing isobutylene according to claim 1, wherein B is niobium.

7. The catalyst for producing isobutylene according to claim 6, wherein a ratio (A/B) of a A of the numbers of moles of tungsten to a total B of the numbers of moles of niobium is from 0.25 to 4.0.

8. The catalyst for producing isobutylene according to claim 1, wherein B is titanium.

9. The catalyst for producing isobutylene according to claim 8, wherein a ratio (A/B) of a A of the numbers of moles of tungsten to a total B of the numbers of moles of titanium is from 2.0 to 8.0.

* * * * *